United States Patent [19]

Mullen

[11] Patent Number: 5,468,473

[45] Date of Patent: Nov. 21, 1995

[54] ANTIPERSPIRANT FOR HANDS AND FEET

[75] Inventor: Patricia Mullen, Babylon, N.Y.

[73] Assignee: Innova Products, Inc., Naples, Fla.

[21] Appl. No.: 194,096

[22] Filed: Feb. 9, 1994

[51] Int. Cl.⁶ .............................. A61K 7/32; A61K 7/34; A61K 7/38; A61K 7/48

[52] U.S. Cl. .......................... 424/66; 424/68; 424/195.1; 514/770; 514/781

[58] Field of Search ................................ 424/68, 67, 66

[56] References Cited

U.S. PATENT DOCUMENTS

| | | | |
|---|---|---|---|
| 3,395,214 | 7/1968 | Mummert | 424/47 |
| 4,383,988 | 5/1983 | Teng et al. | 424/68 |
| 4,605,554 | 8/1986 | Prussin et al. | 424/66 |
| 4,664,909 | 5/1987 | Marschner | 424/65 |
| 4,695,451 | 9/1987 | Straw et al. | 424/47 |

OTHER PUBLICATIONS

Ash, A Formulary of Cosmetic Preparations, 1977, Chemical Publishing Co. Inc. New York, N.Y. pp. 9–15, 24 and 25.
The Essential Oils, Jul. 1932, pp. 554–564 and 764–768.

*Primary Examiner*—Dale R. Ore
*Attorney, Agent, or Firm*—William F. Hamrock

[57] ABSTRACT

An aqueous alcohol carrier solvent based antiperspirant composition which does not contain silicone products and which forms a thick lotion for use on the hands and feet. The composition includes a thickener—absorber mixture of hydroxylalkylcellulose, preferably hydroxypropylmethylcellulose, with colloidal silica and silicates and an antiperspirant active material, preferably chlorhydrol. A preferred embodiment includes the addition of Tea Tree Oil to the formulation. The antiperspirant composition reduces sweating on the hands and feet and is nonirritating, nontacky and mildly soothing to the skin.

14 Claims, No Drawings

ANTIPERSPIRANT FOR HANDS AND FEET

BACKGROUND OF THE INVENTION

1. Field of the Invention

The invention relates to an antiperspirant, named DRY GRIP, to reduce sweating on a person's hands and feet, and more particularly, to a nonirritating antiperspirant thick lotion for the hands and feet having maximum antiperspirant activity at low concentrations.

2. Description of the Prior Art

Various antiperspirant formulations are well known in the cosmetic and chemical literature. Certain ingredients of the formulations are usually present such as inorganic compounds of aluminum, zinc and zirconium having an astringent effect upon the skin which function by closing the pores of the skin that encase sweat glands to limit perspiration. The use of polymeric materials as gelling agents or thickening agents in aqueous antiperspirant compositions is known. U.S. Pat. No. 4,383,988 discloses alcoholic gelled antiperspirant compositions containing hydroxypropyl cellulose acetate as the gelling agent. Cellulose derivatives such as hydroxyalkycelluloses have been disclosed as optional components in gel phases containing monohydric alcohols such as ethanol to help retard alcohol evaporation and to act as an antisyneresis agent. Other ingredients used in antiperspirant compositions include silicone products, talc, sodium bicarbonate, starch, fumed silica and clays. The present composition is different from most of the prior art by not using silicone products in the present formulations.

Almost all of the antiperspirant compositions of the prior art are formulated for application to the various parts of the body in the form of creams, gels, solids, roll-ons or powders. Very few, if any, of these formulations are applicable to the hands, and very few to the feet, for a number of reasons. The main reason is that they are not suitable formulations. For example, some compositions may be tacky and produce aesthetically undesirable high levels of material on the skin. Other compositions may be difficult to apply such as those in powder forms. Some other compositions are not suitable because they irritate sensitive skin areas.

Antiperspirant compositions which contain silicone products are not suitable for application to the hands and feet for various reasons. For example, silicone based antiperspirants are usually tacky and do not dry quickly which characteristics cannot be tolerated for application to the hands and feet. Also, antiperspirant for the hands and feet must spread quickly over the skin and be able to dry quickly during the spreading. Silicone based antiperspirant compositions do not appear to meet these requirements.

There are known antiperspirants compositions for application to the feet. U.S. Pat. 4,954,334 is a foot powder antiperspirant composition containing boric acid and aluminum ammonium sulfate which is sprinkled into the socks. U.S. Pat. 4,777,034 is a foot antiperspirant composition having a large number of ingredients which may be used in various forms. The inventor is not aware of any antiperspirant formulations to be used on the hands.

A person's hands and feet are subject to similar perspiration problems exhibited by other parts of the body. Additionally, the hands and feet are often cracked and dried out which require a mild treating agent and preferably a skin conditioner in addition to the antiperspirant. For example, controlling perspiration of the hands is critical in many occupations and activities such as physically working with the hands, driving vehicles, performing delicate hand operations, most sports activities and in many more areas. Controlling perspiration of the feet is known to be a serious problem for many people. Thus, there does appear to be a need for an antiperspirant composition that meet the needs of many.

Accordingly, it is an object of this invention to provide a unique antiperspirant composition which is an effective antiperspirant on the hands and feet and does not contain silicone products.

It is another object of the invention to provide such a composition which is nontacky and nonirritating when applied to the hands and feet.

It is another object to provide such a composition which is also a skin conditioner as well as an antiperspirant.

It is another object to provide such a composition which is inexpensive and requires only a small amount of material to be effective.

These objects and other objects of the invention will be apparent from the detailed description which follows.

SUMMARY OF THE INVENTION

It has been found that the antiperspirant composition of this invention contains selected thickening and absorbing agents, opacifiers and carrier solvents forming a unique antiperspirant lotion entirely different from the prior art. When applied to the hands and feet, the lotion has good application properties and cosmetic characteristics and is nonirritating and nontacky. In particular, only a small amount of the lotion is required which produces maximum antiperspirant activity at low concentration and it does not develop a tacky feel during dry-down. A preferred composition includes a unique ingredient which provides germicide and fungicide properties in treating skin irritations and infections.

The beneficial objects and advantages of the present invention are accomplished by a lotion composition including thickeners/absorbers such as colloidal silica, bentonite, talc and hydroxyalkyl cellulose, an opacifier of titanium dioxide, carrier solvents of water and alcohol, an antiperspirant active material of chlorhydrol, and fragrance. A very preferred embodiment of the invention is provided when modifying the composition by adding a germicide and fungicide material of Tea Tree Oil with a dispersant and stabilizer of Polysorbate 20. The composition containing Tea Tree Oil has been found to have excellent properties for a hands and feet antiperspirant.

DESCRIPTION OF THE PREFERRED EMBODIMENTS

The preferred antiperspirant basic formulation of the invention is divided into a number of functional components. These include an antiperspirant active material, carrier solvents, thickeners/absorbers, opacifiers, and a fragrance. In addition to these materials, a most unexpected discovery is the inclusion of Tea Tree Oil and Polysorbate 20 in the composition. The Polysorbate 20 acts to increase the dispersability and stability of the Tea Tree Oil. The inclusion of Tea Tree Oil provides unique benefits to the composition not previously seen in other antiperspirant compositions.

The antiperspirant active material useful in the invention includes any material which is antiperspirant active. Generally preferred are the aluminum and zirconium antiperspirant compounds. Most preferred is chlorhydrol which is 5/6 basic aluminum chloride having a relatively high pH, a high aluminum content, a low irritating effect on the skin and an ease of formulating. Chlorhydrol has been found to be the most suitable antiperspirant active material for the present invention at a concentration of about 2.5%.

The carrier solvents used are water and alcohol preferably isopropyl alcohol. This aqueous alcohol solvent combination has been found to be most effective for applying the composition to the hands and feet and facilitates good coverage and rapid drying on the hands and feet. The thickeners/absorbers found to be most useful in the invention are colloidal silicas, bentonite, talc and hydroxyalkylcellulose which produce a thick lotion in combination with the other ingredients of the formulation. The colloidal silica are composed of submicron sized particles with high surface areas less than about one micron in size, preferably a fumed silica. The preferred colloidal silica used is Cab-O-Sil (from Cabot Corporation) having a surface area ranging from about 200 to about 400 square meters per gram. Cab-O-Sil HS-5 has been found to be the most preferred for this lotion when used at a concentration of about 4.5%.

Bentonites are silicate thickening agents which have been found to work well with the ingredients of this aqueous alcohol based lotion. The preferred bentonite is Bentolite H4430 (from Whittaker, Clark & Daniels) and is used at a concentration of about 4.0%.

The talc found to be useful in the present aqueous isopropyl alcohol based lotion is cosmetic talc powder which is a silicate powder. The preferred concentration is about 4.0%.

Hydroxyalkylcellulose are cellulose ether polymers which dissolve or are miscible, in the aqueous alcohol solvents. In the present aqueous isopropyl alcohol solvents based lotion, the polymer found to be most effective is hydroxypropylmethylcellulose and is soluble in the composition. In fact, the preferred polymer acts not only as a thickener but also appears to act as a conditioner for the hands and feet in conjunction with the chlorhydrol antiperspirant compound in the lotion composition. Methocels (Dow Chemical Company) have been found to be the preferred hydroxypropylmethycellulose in the present composition and is used at a concentration of about 0.25%.

The opacifier and fragrance used in the composition can be one or more of those commonly used in antiperspirant compositions. In the present formulation, titanium dioxide as a white pigment at a concentration of about 0.25% has been found to work well as a opacifier in combination with other ingredients of the composition. Likewise, a conventional fragrance or perfume can be used at a concentration of about 0.10%.

A pH of 5.8–6.0 is preferred. It has been found that this pH is most effective in the present formulation when applied to the hands and feet. The potential for irritating the skin of the hands and feet is at its lowest level at this pH.

Sodium hydroxide is the preferred base for adjusting the pH. The sodium hydroxide base also stabilizes and develops the viscosity of the composition from the Methocel.

The most preferred embodiment of the invention results when the composition is modified with Tea Tree Oil. This material makes the antiperspirant formula unique by relating it for use on the hands and feet. Tea Tree Oil also known as Oil of Melaleuca is an oil obtained from the tea tree (Melaleuca alteonifolia) which is found only on the northern seaboard of New South Wales in Australia. It is known as a nontoxic, nonirritating germicide and fungicide for skin complaints. It is also known to exhibit preservative activity. Applicant is not aware of Tea Tree Oil having been used in any marketed product in the antiperspirant or deodorant field. The amount of Tea Tree Oil required for antiperspirant formulations can vary depending upon the application. In the present formulations, it has been found that a concentration of about 5.0% is satisfactory.

When Tea Tree Oil is added to the present aqueous alcohol formulations, it is also necessary to add a material which disperses the oil in the aqueous alcohol system. The preferred dispersing agent is a polysorbate such as Polysorbate 20 which is an emulsifier and surface active agent. Polysorbates are polyoxyethylene derivatives of fatty acids partial esters of sorbitol and hydrides. Polysorbate 20 contains 20 mols of ethylene oxide.

The following formulations have been found to have excellent antiperspirant properties by reducing sweating when applied on the palms of the hands and on the feet.

| DRY GRIP FORMULA I | | |
|---|---|---|
| INGREDIENTS | SUPPLIER | wt. % |
| Deionized Water | | 44.65 |
| Isopropyl Alcohol | | 13.00 |
| Chlorhydrol 60% Solution | Reheis | 4.50 (2.70 Chlorhydrol) |
| Cab-O-Sil HS-5 | Cabot | 4.50 |
| Bentolite H-4430 | Whittaker, Clark & Daniels | 4.00 |
| Talc | Whittaker, Clark & Daniels | 4.00 |
| Methocel EM4 (1% Soln.) | Dow Chemical | 25.00 (0.25 Methocel EM4) |
| Titanium Dioxide | Whittaker, Clark & Daniels | 0.25 |
| Perfume | IPC | 0.10 |
| Sodium Hydroxide 50% Solution Adjust pH to 5.8–6.0 | | |
| TOTAL | | 100.00% |

Formula I was prepared as follows:

1. Prepare the 1% solution of Methocel,
2. Into a suitable container weigh water, heat to 80–850 C. and sprinkle in Bentolite with high speed shear mixing until uniform.
3. Add Cab-O-Sil and IPA to Bentolite and mix well until uniform.
4. Add talc and Titanium Dioxide followed by Chlorhydrol. Mix until uniform.
5. Pour in Methocel solution and mix. Base will thin out.
6. Adjust pH with Sodium Hydroxide solution. Base will thicken.
7. Add Perfume. Mix until uniform.
8. Package.

Formula I was prepared in the laboratory. The composition produced is a low cost, nonirritating antiperspirant thick lotion having good antiperspirant activity on the hands and feet at low concentration.

DRY GRIP FORMULA II

Formula modification necessitated the use of a homogenizer in the addition of the Talc and Titanium Dioxide.

| INGREDIENTS | SUPPLIER | wt. % |
|---|---|---|
| Deionized Water | | 51.34 |
| Isopropyl Alcohol | | 14.95 |
| Chlorhydrol 50% Solution | Reheis | 4.50 (2.25 Chlorhydrol) |
| Cab-O-Sil HS-5 | Cabot | 4.50 |
| Bentolite H-4430 | Whittaker, Clark & Daniels | 4.00 |
| Talc | Whittaker, Clark & Daniels | 4.00 |
| Methocel EM4 (1% Soln.) | Dow Chemical | 16.35 (0.16 Methocel EM4) |
| Titanium Dioxide | Whittaker, Clark | 0.25 |
| Perfume | IPC | 0.10 |
| Sodium Hydroxide 50% Solution, Adjust pH to 5.8–6.0 | | |
| TOTAL | | 100.00% |

COMPOUNDING PROCEDURE

1. Prepare the 1% solution of Methocel.
2. Into a suitable container weigh water, heat to 80–85 C. and sprinkle in Bentolite with high speed shear mixing until uniform.
3. Add Cab-O-Sil and IPA to Bentolite and mix well until uniform.
4. Add Talc and titanium Dioxide and mix with a homogenizer. Add Chlorhydrol. Mix until uniform.
5. Pour in Methocel solution and mix. Base will thin out.
6. Adjust pH with Sodium Hydroxide solution. Base will thicken.
7. Add Perfume. Mix until uniform.
8. Package.

Formula II was prepared under industrial conditions. It has good antiperspirant properties when applied to the hands and feet.

| DRY GRIP FORMULA III | |
|---|---|
| INGREDIENTS | WT. % |
| Deionized Water | 43.65 |
| Isopropyl Alcohol | 12.75 |
| Chlorhydrol 50% Solution | 3.50 (1.75 Chlorhydrol) |
| Cab-O-Sil HS-5 | 3.50 |
| Bentolite H-4430 | 3.00 |
| Talc 1623 | 3.00 |
| Methocel 40-202 (1% Solution) | 15.25 (0.15 Methocel 40-202) |
| Titanium Dioxide | 0.25 |
| Tea Tree Oil | 5.00 |
| Polysorbate 20 | 10.00 |
| Perfume | 0.10 |
| Sodium Hydroxide (50% solution), pH 5.8–6.0 | |

COMPOUNDING PROCEDURE

Same as previous except:
6. Premix Tea Tree Oil and Polysorbate 20. Add to batch.
7. Adjust pH with Sodium Hydroxide solution. Base should thicken.
8, Add perfume and package in tubes.

Formula III includes the addition of Tea Tree Oil and Polysorbate 20 in the formula.

Although the present invention has been described in detail with reference to a particular preferred embodiment, persons possessing ordinary skill in the art to which this invention pertains will appreciate that various modifications and enhancements may be made without departing from the spirit and scope of the invention.

What is claimed is:

1. A low concentration antiperspirant lotion composition for the hands and feet based upon about 100% by weight of the composition containing no silicone products comprising,
   (a) an effective amount of an aqueous alcohol carrier solvent,
   (b) an effective amount of a thickener—absorber mixture of about 0.25% 0.16% or 0.15% by weight hydroxylalkylcellulose in combination with about 4.5% or 3.5% by weight colloidal silica and at least one silicate of about 4.0% or 3.0% by weight, and
   (c) an effective amount of about 2.7% 2.5% 2.25% or 1.75% by weight of an aluminum or zirconium antiperspirant active material,
   wherein the lotion composition has a pH of about 5.8 to 6.0.

2. An antiperspirant lotion composition according to claim 1 wherein the hydroxyalkylcellulose is hydroxypropylmethylcellulose.

3. An antiperspirant lotion composition according to claim 2 wherein the amount of hydroxypropylmethylcellulose is about 0.25% by weight.

4. An antiperspirant according to claim 3 wherein the antiperspirant active material is chlorhydrol.

5. An antiperspirant lotion composition according to claim 4 wherein the amount of chorhydrol is about 2.25% by weight.

6. An antiperspirant lotion composition according to claim 5 wherein the amount of colloidal silica is about 4.5% by weight.

7. An antiperspirant lotion composition according to claim 6 wherein two silicates are used in an amount of about 4.0% by weight for each.

8. An antiperspirant lotion composition according to claim 1 containing Tea Tree Oil.

9. An antiperspirant lotion composition according to claim 8 containing an effective amount of a polysorbate dispersing agent.

10. An antiperspirant lotion composition according to claim 9 wherein the Tea Tree Oil is used in an amount of about 5.0% by weight.

11. An antiperspirant lotion composition according to claim 7 wherein said silicates are bentonite and talc.

12. An antiperspirant lotion composition according to claim 11 wherein the composition includes about 0.25% by weight of titanium dioxide.

13. An antiperspirant lotion composition according to claim 12 wherein the composition includes about 0.10% by weight of a perfume.

14. An antiperspirant lotion composition according to claim 10 wherein the polysorbate dispersing agent is used in an amount of about 10% by weight.

* * * * *